(12) United States Patent
Rostami et al.

(10) Patent No.: US 6,433,221 B1
(45) Date of Patent: *Aug. 13, 2002

(54) METHODS OF SEPARATING CATALYST IN SOLUTION FROM A REACTION MIXTURE PRODUCED BY OXIDATION OF CYCLOHEXANE TO ADIPIC ACID

(75) Inventors: Ader M. Rostami; Douglas J. Dudgeon, both of Bainbridge Island; David C. DeCoster, Buckley; Mark W. Dassel, Indianola, all of WA (US); Eustathios Vassiliou, Newark, DE (US)

(73) Assignee: RPC Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/345,693

(22) Filed: Jun. 30, 1999

Related U.S. Application Data

(60) Provisional application No. 60/111,848, filed on Dec. 11, 1998, provisional application No. 60/110,206, filed on Nov. 30, 1998, provisional application No. 60/105,048, filed on Oct. 20, 1998, provisional application No. 60/093,256, filed on Jul. 17, 1998, and provisional application No. 60/091,483, filed on Jul. 2, 1998.

(51) Int. Cl.$^7$ .............................................. C07C 51/31

(52) U.S. Cl. ........................ 562/543; 562/590; 562/593

(58) Field of Search ................................ 562/543, 590, 562/593

(56) References Cited

U.S. PATENT DOCUMENTS

| | | | |
|---|---|---|---|
| 1,121,532 A | 12/1914 | Newberry | |
| 1,867,933 A | 7/1932 | Wilton | |
| 2,014,044 A | 9/1935 | Haswell | ........................ 75/17 |
| 2,223,493 A | * 12/1940 | Loder | ........................ 562/543 |

(List continued on next page.)

FOREIGN PATENT DOCUMENTS

| | | |
|---|---|---|
| DE | 2 309 423 | 8/1974 |
| DE | 4426132 A1 | 1/1996 |
| DE | 4427474 A1 | 2/1996 |

(List continued on next page.)

OTHER PUBLICATIONS

E. Sorribes et al., "Formación de nuevas fases en el proceso de obtención de ácido adípico: causas y efectos que provocan," *Rev. R. Acad. Cienc. Exactas, Fis. Nat. Madrid* (1987), 81 (1), 233–5 (+ English language translation).

Lewis, *Hawley's Condensed Chemical Dictionary*, 12$^{th}$ ed., 1993, pp. 7, 336, and 1076.

Primary Examiner—Paul J. Killos
Assistant Examiner—Taylor V Oh
(74) Attorney, Agent, or Firm—Seed Intellectual Property Law Group PLLC

(57) ABSTRACT

This invention relates to methods of controlling the oxidation of cyclohexane to adipic acid in the presence of a monobasic acid solvent, by separating the catalyst from the reaction mixture, outside the reaction zone. Substantially all the unreacted cyclohexane, the majority of adipic acid, and substantially all the monobasic acid solvent are preferably removed. A protic solvent, may be added intermittently or continuously in the reaction mixture during the removal of the monobasic acid solvent, preferably by distillation, for preventing solids precipitation. A dipolar aprotic solvent is then added in the presence of an adequate amount of the protic solvent to maintain a single liquid phase, followed by a step of formation of two liquid phases, a solids-free protic liquid phase containing substantially all the catalyst, and a solids-free aprotic liquid phase containing at least the majority of ingredients of the reaction mixture. The formation of the two phases is performed by a process selected from a group consisting of lowering the first temperature to a second temperature, adding additional protic solvent, adding an apolar aprotic solvent, and a combination thereof.

36 Claims, 1 Drawing Sheet

U.S. PATENT DOCUMENTS

| | | | |
|---|---|---|---|
| 2,223,494 A | 12/1940 | Loder et al. | 260/586 |
| 2,301,240 A | 11/1942 | Baumann et al. | 183/115 |
| 2,439,513 A | 4/1948 | Hamblet et al. | 260/533 |
| 2,557,282 A | 6/1951 | Hamblet et al. | 260/533 |
| 2,565,087 A | 8/1951 | Porter et al. | 260/631 |
| 2,980,523 A | 4/1961 | Dille et al. | 48/215 |
| 3,161,603 A | 12/1964 | Leyshon et al. | 252/413 |
| 3,231,608 A | 1/1966 | Kollar | 260/533 |
| 3,234,271 A | 2/1966 | Barker et al. | 260/531 |
| 3,290,369 A | 12/1966 | Bonfield et al. | 260/537 |
| 3,361,806 A | 1/1968 | Lidov | 260/531 |
| 3,386,810 A | 6/1968 | Burke, Jr. et al. | 23/285 |
| 3,390,174 A | 6/1968 | Schulz et al. | 260/533 |
| 3,515,751 A | 6/1970 | Oberster et al. | 260/533 |
| 3,522,018 A | 7/1970 | Bachmann et al. | 23/285 |
| 3,530,185 A | 9/1970 | Pugi | 260/586 |
| 3,613,333 A | 10/1971 | Gardenier | 55/89 |
| 3,649,685 A | 3/1972 | Ishimoto et al. | 260/533 C |
| 3,677,696 A | 7/1972 | Bryk et al. | 23/2 |
| 3,786,096 A | 1/1974 | Konno | 260/537 R |
| 3,819,813 A | 6/1974 | Jones, Jr. et al. | 423/421 |
| 3,839,435 A | 10/1974 | Shigeyasu et al. | 260/524 R |
| 3,869,508 A | 3/1975 | Longley et al. | 260/531 R |
| 3,928,005 A | 12/1975 | Laslo | 55/73 |
| 3,932,513 A | 1/1976 | Russell | 260/586 AB |
| 3,946,076 A | 3/1976 | Paasen et al. | 260/586 P |
| 3,957,876 A | 5/1976 | Rapoport et al. | 260/586 P |
| 3,987,100 A | 10/1976 | Barnette et al. | 260/586 P |
| 3,987,808 A | 10/1976 | Carbonell et al. | 137/3 |
| 4,025,498 A | 5/1977 | Buss et al. | 260/95 A |
| 4,032,569 A | 6/1977 | Onopchenko et al. | 260/533 C |
| 4,039,304 A | 8/1977 | Bechthold et al. | 55/10 |
| 4,055,600 A | 10/1977 | Langley et al. | 260/586 P |
| 4,065,527 A | 12/1977 | Graber | 261/79 A |
| 4,158,739 A | 6/1979 | Schulz et al. | 562/543 |
| 4,160,108 A | 7/1979 | Shigeyasu et al. | 562/416 |
| 4,161,573 A | 7/1979 | Gunsher et al. | 526/64 |
| 4,200,617 A | 4/1980 | Levy | 422/198 |
| 4,263,453 A | 4/1981 | Schulz et al. | 562/543 |
| 4,269,805 A | 5/1981 | Schoengen et al. | 422/106 |
| 4,279,846 A | 7/1981 | Ishii et al. | 264/41 |
| 4,308,037 A | 12/1981 | Meissner et al. | 55/10 |
| 4,332,590 A | 6/1982 | Smith | 23/230 A |
| 4,361,965 A | 12/1982 | Goumondy et al. | 34/57 R |
| 4,370,304 A | 1/1983 | Hendriks et al. | 422/224 |
| 4,394,139 A | 7/1983 | Board | 55/20 |
| 4,419,184 A | 12/1983 | Backlund | 162/49 |
| 4,423,018 A | 12/1983 | Lester, Jr. et al. | 423/243 |
| 4,477,380 A | 10/1984 | Knips et al. | 260/386 |
| 4,543,399 A | 9/1985 | Jenkins, III et al. | 526/70 |
| 4,588,790 A | 5/1986 | Jenkins, III et al. | 526/70 |
| 4,603,220 A | 7/1986 | Feld | 562/416 |
| 4,902,827 A | 2/1990 | Steinmetz et al. | 562/543 |
| 4,989,452 A | 2/1991 | Toon et al. | 73/293 |
| 5,061,453 A | 10/1991 | Krippl et al. | 422/106 |
| 5,104,492 A | 4/1992 | King et al. | 203/15 |
| 5,117,007 A | 5/1992 | Taheri | 549/259 |
| 5,123,936 A | 6/1992 | Stone et al. | 55/8 |
| 5,139,753 A | 8/1992 | Hardison | 423/220 |
| 5,170,727 A | 12/1992 | Nielsen | 110/346 |
| 5,206,701 A | 4/1993 | Taylor et al. | 356/325 |
| 5,221,800 A | 6/1993 | Park et al. | 562/543 |
| 5,244,603 A | 9/1993 | Davis | 261/87 |
| 5,259,996 A | 11/1993 | Morgan | 261/114.1 |
| 5,270,019 A | 12/1993 | Melton et al. | 422/234 |
| 5,271,904 A | 12/1993 | Esposito et al. | 422/105 |
| 5,286,458 A | 2/1994 | Yang et al. | 422/168 |
| 5,294,378 A | 3/1994 | Succi et al. | 261/130 |
| 5,312,567 A | 5/1994 | Kozma et al. | 261/87 |
| 5,321,157 A | 6/1994 | Kollar | 562/543 |
| 5,374,767 A | 12/1994 | Drinkard et al. | 560/193 |
| 5,396,850 A | 3/1995 | Conochie et al. | 110/346 |
| 5,399,750 A | 3/1995 | Brun et al. | 562/553 |
| 5,463,119 A | 10/1995 | Kollar | 562/543 |
| 5,502,245 A | 3/1996 | Dassel et al. | 562/413 |
| 5,505,920 A | 4/1996 | Kollar et al. | 423/246 |
| 5,516,423 A | 5/1996 | Conoby et al. | 210/85 |
| 5,547,905 A | 8/1996 | Kulsrestha et al. | 502/66 |
| 5,558,842 A | 9/1996 | Vassiliou et al. | 422/108 |
| 5,580,531 A | 12/1996 | Vassiliou et al. | 422/108 |
| 5,654,475 A | 8/1997 | Vassiliou et al. | 562/413 |
| 5,756,837 A * | 5/1998 | Costantini et al. | 562/543 |
| 5,801,273 A | 9/1998 | Vassiliou et al. | 562/413 |
| 5,801,282 A | 9/1998 | Dassel et al. | 562/413 |
| 5,817,868 A | 10/1998 | Rostami et al. | 562/413 |
| 5,824,819 A | 10/1998 | Dassel et al. | 562/529 |
| 5,877,341 A | 3/1999 | Vassiliou et al. | 560/77 |
| 5,883,292 A | 3/1999 | Dassel et al. | 562/413 |
| 5,908,589 A | 6/1999 | DeCoster et al. | 264/37.18 |
| 5,922,908 A | 7/1999 | Dassel et al. | 562/543 |
| 5,929,277 A | 7/1999 | DeCoster et al. | 562/593 |

FOREIGN PATENT DOCUMENTS

| | | |
|---|---|---|
| EP | 439 007 A2 | 7/1991 |
| EP | 494 416 A2 | 7/1992 |
| EP | 729 084 A1 | 8/1996 |
| EP | 729 085 A1 | 8/1996 |
| EP | 751 105 A2 | 1/1997 |
| FR | 2 722 783 A1 | 1/1996 |
| GB | 415172 | 8/1934 |
| GB | 738808 | 10/1955 |
| GB | 864106 | 3/1961 |
| GB | 1143213 | 2/1969 |
| GB | 2 014 473 A | 8/1979 |
| GB | 2 072 667 A | 10/1981 |
| JP | 48-003815 | 2/1973 |
| JP | 50034006 B | 11/1975 |
| JP | 54-33891 | 3/1979 |
| JP | 61 063634 | 4/1986 |
| WO | WO 94/07833 | 4/1994 |
| WO | WO 94/07834 | 4/1994 |
| WO | WO94/07834 * | 4/1994 |
| WO | WO 96/03365 | 2/1996 |
| WO | WO 96/14288 | 5/1996 |
| WO | WO 96/40610 | 12/1996 |
| WO | WO 97/49485 | 12/1997 |

* cited by examiner

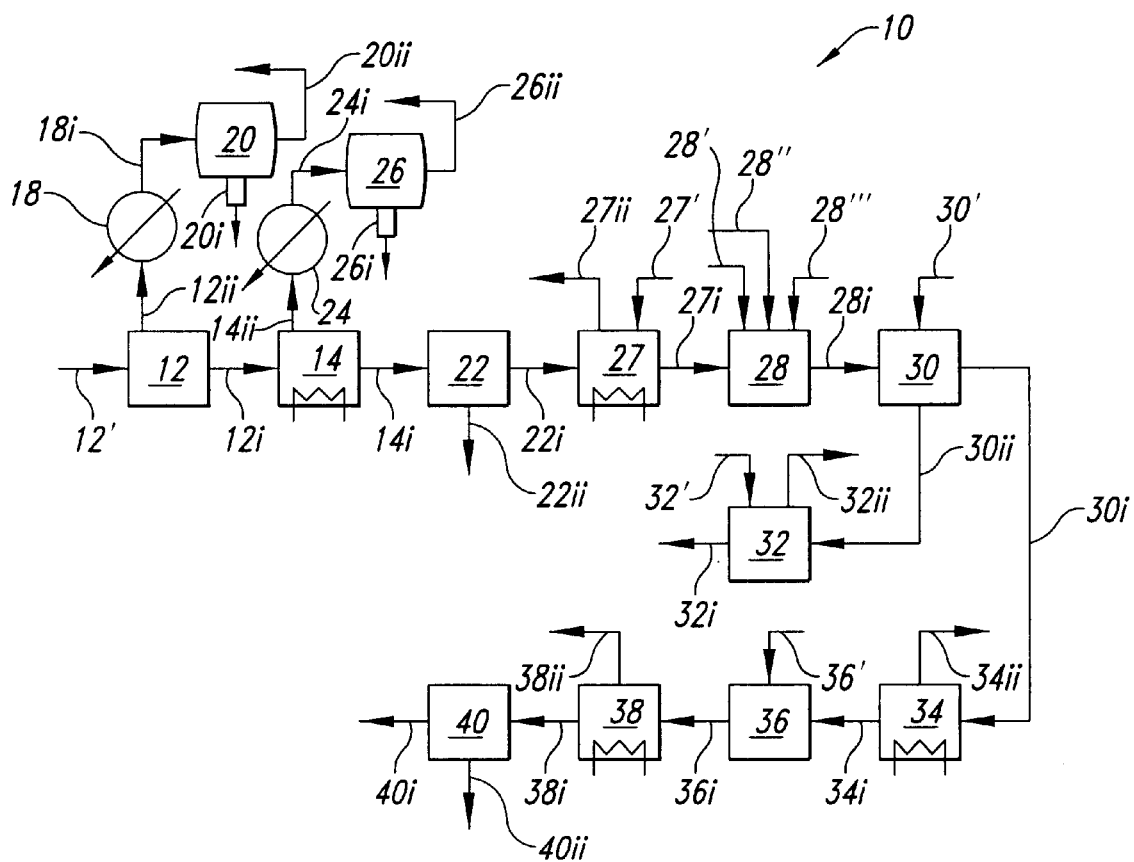

METHODS OF SEPARATING CATALYST IN SOLUTION FROM A REACTION MIXTURE PRODUCED BY OXIDATION OF CYCLOHEXANE TO ADIPIC ACID

CROSS REFERENCE TO RELATED APPLICATIONS

This applications claims from U.S. Provisional Applications No. 60/091,483, filed Jul. 2, 1998, No. 60/093,256, filed Jul. 17, 1998, No. 60/105,048, filed Oct. 20, 1998, No. 60/110,206, filed Nov. 30. 1998, and No. 60/111,848, filed Dec. 11, 1998, all of which applications are incorporated herein by reference in their entirety.

FIELD OF THE INVENTION

This invention relates to method of oxidizing cyclohexane to adipic acid and more specifically, how to remove catalyst as a solution after the reaction, preferably for recycling.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and the oxidation of the KA mixture with nitric acid to adipic acid. Other processes include, among others, the "Hydroperoxide Process," the "Boric Acid Process," and "Direct Synthesis Process," which involves direct oxidation of cyclonexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar" phase and the "Non-Polar" or "Apolar" phase. However, no attention has been paid so far to the importance of the two phases, except for separating the adipic from the "Polar" phase and recycling these phases to the reactor partially or totally with or without further treatment.

In more general nomenclature of phases, "polar phase" is the more polar phase, while "non-polar" or "apolar" phase is the less polar phase.

It is also important to note that most studies on the Direct Synthesis have been conducted in a batch mode, literally or for all practical purposes.

As aforementioned, there is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among others, may be considered as representative of oxidation processes relative to the preparation of diacids and other intermediate oxidation products.

U.S. Pat. No. 5,463,119 (Kollar) discloses a process for the oxidative preparation of C5–C8 aliphatic dibasic acids by
  (1) reacting,
    (a) at least one saturated cycloaliphatic hydrocarbon having from 5 to 8 ring carbon atoms in the liquid phase and
    (b) an excess of oxygen gas or an oxygen-containing gas in the presence of
    (c) a solvent comprising an organic acid containing only primary and/or secondary hydrogen atoms and
    (d) at least about 0.002 mole per 1000 grams of reaction mixture of a polyvalent heavy metal catalyst;
  (2) removing the aliphatic dibasic acid; and
  (3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of C5–C8 aliphatic dibasic acids through oxidation of corresponding saturated cycloaliphatic hydrocarbons by
  (1) reacting, at a cycloaliphatic hydrocarbon conversion level of between about 7% and about 30%,
    (a) at least one saturated cycloaliphatic hydrocarbon having from 5 to 8 ring carbon atoms in the liquid phase and
    (b) an excess of oxygen gas or an oxygen containing gas mixture in the presence of
    (c) less than 1.5 moles of a solvent per mole of cycloaliphatic hydrocarbon (a), wherein said solvent comprises an organic acid containing only primary and/or secondary hydrogen atoms and
    (d) at least about 0.002 mole per 1000 grams of reaction mixture of a polyvalent heavy metal catalyst; and
  (2) isolating the C5–C8 aliphatic dibasic acid.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° C. to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3–0.7%.

PCT International Publication WO 96/03365 and U.S. Pat. No. 5,756,837 (both of Costantini et al.) disclose a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

German Patent Publication DE 44 27 474 A1 (Ohst et al.) discloses a method consisting of cooling the reaction mixture, separating the precipitated adipic acid by filtration, separating the filtrate into a polar and a non-polar phase, a portion of which polar phase is extracted, and the catalyst present in this portion is recovered (a) by mixing with cyclohexanone, followed by removal by distillation of the acetic acid present and filtration; or (b) by removal by distillation of the majority of the acetic acid present, hydrolytic decomposition of the distillation residue, and extraction in the form of an aqueous solution of the organic constituents then present with the exception of the catalyst. None of the above references, or any other references known to the inventors disclose, suggest or imply, singly or in combination, control of oxidation reactions subject to the intricate and critical controls and requirements of the instant invention as described and claimed.

Our U.S. Pat. Nos. 5,654,475, 5,580,531, 5,558,842, 5,502,245, 5,801,282, and co-pending application Ser. No. 08/587,967, filed on Jan. 17, 1996, all of which are incorporated herein by reference, describe methods and apparatuses relative to controlling reactions in atomized liquids. In addition, our U.S. Pat. Nos. 5,801,273 and 5,817,868, and the following co-pending U.S. applications are also incorporated herein by reference: Ser. No. 08/812,847, filed on Mar. 6, 1997; Ser. No. 08/824,992, filed on Mar. 27, 1997; Ser. No. 08/861,281 filed on May 21, 1997; Ser. No. 08/861,180 filed on May 21, 1997; Ser. No. 08/861,176 filed on May 21, 1997; Ser. No. 08/861,210 filed on May 21, 1997; Ser. No. 08/876,692, filed on Jun. 16, 1997; Ser. No. 08/900,323, filed on Jul. 25, 1997; Ser. No. 08/931,035, filed on Sep. 16, 1997; Ser. No. 08/932,875 filed on Sep. 18, 1997; Ser. No. 08/934,253, filed on Sep. 19, 1997; Ser. No. 08/986,505, filed on Dec. 8, 1997; Ser. No. 08/989,910, filed on Dec. 12, 1997; No. 60/074,068, filed on Feb. 9, 1998; No. 60/075,257, filed Feb. 19, 1998; No. 60/086,159, filed May 20, 1998; No. 60/086,119, filed May 20, 1998; No. 60/086,118, filed May 20, 1998; No. 60/091,483, filed on Jul. 2, 1998.

SUMMARY OF THE INVENTION

As aforementioned, this invention relates to methods of oxidizing hydrocarbons, such as cyclohexane for example, to respective intermediate oxidation products, such as adipic acid for example, and more specifically, how to remove catalyst in solution after the reaction, preferably for recycling. More particularly, this invention pertains a method of treating a reaction mixture produced by direct oxidation of cyclohexane to adipic acid, the reaction mixture comprising cyclohexane, adipic acid, a monobasic acid solvent having only primary and/or secondary hydrogen atoms, optionally water, and a metal ion catalyst, the method being characterized by steps of:

(a) removing substantially the totality of the cyclohexane;

(b) removing a major part of the adipic acid;

(c) removing substantially the totality of the monobasic acid solvent by distillation, during which a protic solvent is added continuously or intermittently in an adequate amount substantially to prevent solids precipitation, to provide a first single liquid phase, the first single liquid phase being homogeneous and solids-free, the protic solvent containing no carboxylic or mineral acid groups and having a normalized solvent polarity parameter EN in the range of 0.9 to 1.0;

(d) adding to the first single liquid phase a dipolar aprotic solvent and, if needed, additional protic solvent, in such quantities so as to provide a second single liquid phase that is homogeneous and solids-free at a desired first temperature, the dipolar aprotic solvent having a normalized solvent polarity parameter $E_N$ in the range of 0.2 to 0.4;

(e) causing formation of two liquid phases, a solids-free protic liquid phase containing substantially all the metal ion catalyst, and a solids-free aprotic liquid phase containing at least the majority of ingredients of the reaction mixture, by a process selected from a group consisting of lowering the first temperature to a second temperature, adding additional protic solvent, adding an apolar aprotic solvent having a $E_N$ value in the range of 0.0 to 0.1, and a combination thereof; and (f) separating the solids-free protic liquid phase containing the catalyst from the solids-free aprotic liquid phase; wherein $E_N$ is defined by equation (1)

$$E_N = \frac{E_T(\text{solvent}) - E_T(\text{TMS})}{E_T(\text{water}) - E_T(\text{TMS})} = \frac{E_T(\text{solvent}) - 30.7}{32.4} \quad (1)$$

using water and tetramethylsilane as extreme reference solvents, such that $E_T$(solvent) is the $E_T$ value corresponding to the solvent under consideration, $E_T$(TMS) is the $E_T$ value corresponding to tetramethylsilane, and $E_T$(water) is the $E_T$ value corresponding to water, and wherein $E_T$ is defined by equation (2)

$$E_T/(\text{kcal·mol}^{-1}) = h \cdot c \cdot v \cdot N_A = 2.859 \times 10^{-3} \cdot v/\text{cm}^{-1} \quad (2)$$

in which v is the wavenumber ($\text{cm}^{-1}$) of the photon which produces the electronic excitation, h is Plank's constant, c is the velocity of light, and $N_A$ is Avogadro's Number, $E_T$ being based either directly on the transition energy for the longest wavelength solvatochromic absorption band of pyridinium-N-phenoxide betaine dye in the solvent under consideration, or indirectly by the use of the more lipophilic penta-tert-butyl-substituted pyridinium-N-phenoxide betaine dye in the solvent under consideration.

Further, the present invention is related to a method of separating catalyst in a solution form from a reaction mixture produced by direct oxidation of cyclohexane to adipic acid, the reaction mixture comprising cyclohexane, adipic acid, a monobasic acid solvent having only primary and/or secondary hydrogen atoms, optionally water, and a metal ion catalyst, the method being characterized by steps of:

(a) removing substantially the totality of the cyclohexane;

(b) optionally removing a major part of the adipic acid;

(c) forming a first solids-free single liquid phase containing less than about 20% by weight monobasic acid solvent by removing an adequate amount of said monobasic acid solvent;

(d) adding, to the first single liquid phase, a dipolar aprotic solvent and, if needed, additional protic solvent, in such quantities so as to provide a second single liquid phase that is homogeneous and solids-free at a desired first temperature, the dipolar aprotic solvent having a normalized solvent polarity parameter $E_N$ in the range of 0.2 to 0.4;

(e) causing formation of two liquid phases, a solids-free protic liquid phase containing substantially all the metal ion catalyst, and a solids-free aprotic liquid phase containing at least the majority of ingredients of the reaction mixture by a process selected from a group consisting of lowering the first temperature to a second temperature, adding additional protic solvent, adding an apolar aprotic solvent having a $E_N$ value in the range of 0.0 to 0.1, and a combination thereof; and (f) separating the solids-free protic liquid phase containing the catalyst from the solids-free aprotic liquid phase;

The weight ratio of the first single liquid phase to the total protic solvent used in steps (c), and (d), is preferably in the range of 1 to 3. Also, the weight ratio of the dipolar aprotic solvent used in steps (c) and (d) to the first single liquid phase is preferably in the range of 1 to 3.

The first temperature is preferably in the range of 80 to 120° C., and more preferably in the range of 90 to 110° C., while the second temperature is in the range of preferably 15 to 50° C., more preferably 20 to 40° C., and even more preferably 20 to 30° C.

Steps (a) and (b) preferably precede steps (c), (d), (e), and (f).

The method may further comprise a step of recycling the solids-free protic liquid phase to a reaction zone, in which reaction zone cyclohexane is oxidized to adipic acid, either directly or indirectly, and/or with or without removal of protic solvent, and/or with or without addition of monobasic acid solvent.

The method may also comprise a step of hydrolyzing esters contained in the solids-free aprotic liquid phase.

The methods of this invention are particularly applicable in the case that the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

The methods of the invention may further comprise a step of reacting the adipic acid with a reactant selected from a group consisting of a polyol, a polyamine, and a polyamide in a manner to form a polymer of a polyester, or a polyamide, or a (polyimide and/or polyamideimide), respectively. In addition, the method may also comprise a step of spinning the polymer into fibers, and/or adding to the polymer fillers and/or other additives to form composites.

BRIEF DESCRIPTION OF THE DRAWING

The reader's understanding of this invention will be enhanced by reference to the following detailed description taken in combination with the drawing figure, wherein:

FIG. 1 illustrates a block diagram of a preferred embodiment of the present invention

DETAILED DESCRIPTION OF THE INVENTION

As aforementioned, this invention relates to methods of oxidizing cyclohexane to adipic acid for example, and more specifically, how to remove catalyst in solution after the reaction, preferably for recycling.

Proper catalyst handling in oxidation reactions has always been a considerable problem in the art. In the present state of the art, the catalyst may be separated in the form of a solid precipitate. According to the present invention, the catalyst is separated in a liquid form dissolved in a liquid protic phase, and preferably returned to the reaction chamber with or without any further treatment. Separation of the catalyst in solution, especially concentrated solution, is vital, as it does not have the disadvantages of handling solids within liquids. These disadvantages include but are not limited to plugging problems, filtration and/or centrifugation necessity, complex transfer equipment, etc.

Therefore solvation of miscellaneous species in solvents is a critical aspect of this invention.

Solvents may be characterized by their polarity. There is a plethora of references dealing with different methods of measuring polarity. A rather general classification may consist of three broad categories; protic solvents, dipolar aprotic solvents, and apolar aprotic solvents. Protic solvents, such as for example water, alcohols, and carboxylic acids, have high polarity and they are hydrogen bond donors. Dipolar aprotic solvents, such as for example ketones, sulfones, sulfoxides, and nitrites, have a medium polarity, and they are not hydrogen bond donors. Apolar aprotic solvents, such as for example aliphatic, cycloaliphatic, and aromatic hydrocarbons, have very low to negligible polarity, and they are not hydrogen bond donors.

Use of solvatochromic dyes, such as pyridinium-N-phenoxide betaine dye, or the more lipophilic penta-tert-butylsubstituted pyridinium-N-phenoxide betaine dye, can be used to determine a solvent polarity parameter $E_T$, and especially a normalized solvent polarity parameter EN, which differentiate the miscellaneous solvents in a rather sensitive and accurate mode, wherein higher numbers indicate higher polarity and vice versa. One major advantage of this approach is that the solvatochromic absorption is observed at rather long wavelengths in the visible region of the spectrum, from $\lambda=810$ nm, $E_T=35.3$ kcal/mol, in the case of diphenyl ether to $\lambda=453$ nm, $E_T=63.1$ kcal/mol, in the case of water.

The pyridinium-N-phenoxide betaine dye may preferably be used for more polar solvents, while the more lipophilic penta-tert-butylsubstituted pyridinium-N-phenoxide betaine dye, can be used for less polar substances. The two can then be correlated to each other.

As mentioned earlier, $E_N$ is defined according to the equation $$E_N = \frac{E_T(\text{solvent}) - E_T(\text{TMS})}{E_T(\text{water}) - E_T(\text{TMS})} = \frac{E_T(\text{solvent}) - 30.7}{32.4} \quad (1)$$

using water and tetramethylsilane as extreme reference solvents, wherein $E_T$ (solvent) is the $E_T$ value corresponding to the solvent under consideration, $E_T$ (TMS) is the $E_T$ value corresponding to tetramethylsilane, and $E_T$ (water) is the $E_T$ value corresponding to water, $E_T$ is in turn defined from the equation $$E_T/(\text{kcal·mol}^{-1}) = h \cdot c \cdot v \cdot N_A = 2.859 \times 10^{-3} \cdot v/\text{cm}^{-1} \quad (2)$$

in which h is Plank's constant, c is the velocity of light, v is the wavenumber (cm$^{-1}$) of the photon which produces the electronic excitation, and $N_A$ is Avogadro's Number, $E_T$ being based either directly on the transition energy for the longest wavelength solvatochromic absorption band of pyridinium-N-phenoxide betaine dye in the solvent under consideration, or indirectly by the use of the more lipophilic penta-tert-butyl-substituted pyridinium-N-phenoxide betaine dye in the solvent under consideration.

A detailed discussion regarding the solvent polarity parameter and the normalized solvent polarity parameter is given in "Solvents and Solvent Effects in Organic Chemistry", second revised and enlarged edition, by Christian Reichardt, 1988, pp. 69–71 and 359–371, VCH Publishers, 220 East 23$^{rd}$ Street, New York, N.Y. 10010-4606. The above reference is incorporated herein by reference. Examples of $E_N$ values for some solvents are given in Table I. Further details are also given in the references listed below, all of which are incorporated herein by reference.

A. J. Parker, Quart. Rev. (London) 16, 163 (1962)

K. Dimroth, C. Reichardt, T. Sipemann, and F. Bohlmann, Liebigs Ann. Chem. 661, 1 (1963); C. Reichardt, ibid. 752, 64 (1971).

K. Dimroth and C. Reichardt, Z. Anal. Chem. 215, 344 (1966); Z. B. Maksimovic, C. Reichardt, and A. Spirić, ibid. 270, 100 (1974).

T. G. Beaumont and K. M. C. Davis, J. Chem. Soc., Part B 1968, 1010 (dichloromethane-acetonitrile mixtures).

W. Koehler, P. Froelich, and R. Radeglia, Z. Phys. Chem. (Leipzig) 242, 220 (1969) (acetone-, 1,4-dioxane- and tetrahydrofuran-water mixtures).

K. Tamura, Y. Ogo, and T. inoto, Bull. Chem. Soc. Jpn. 46, 2988 (1973) (nitrobenzene-benzene mixtures).

E. M. Kosower, H. Dodiuk, K. Tanizawa, M. Ottolenghi, and N. Orbach, J. Am. Chem. Soc. 97, 2167 (1975) (1,4-dioxane-water mixtures).

C. Reichardt: *Empirical Parameters of Solvent Polarity and Chemical Reactivity.*

C. Reichardt and E. Harbusch-Görnert, Liebigs Ann. Chem. 1983, 721.

C. Laurence, P. Nicolet, and C. Reichardt, Bull. Soc. Chim. Fr. 1987, 125.

C. Laurence, P. Nicolet, M. Lucon, and C. Reichardt, Bull. Soc. Chim, Fr. 1987, 1001.

Y. Marcus: *Ion Solvation.* Chapter 7, Table 7.3 on page 188, Wiley, New York 1985.

T. M. Krygowski, P. K. Wrona, U. Zielkowska, and C. Reichardt, Tetrahedron 41, 4519 (1985).

M. De Vijlder, Bull. Soc. Chim. Belge 91, 947 (1982).

J. R. Haak and J. B. F. N. Engberts, Rec. Trav. Chim. Pays-Bas 105, 307 (1986).

B. P. Johnson, M. G. Khaledi, and J. G. Dorsey, J. Chromatogr. 384, 221 (1987).

J. V. Jouanne, D. A. Pahner, and H. Kehn, Bull. Chem. Soc. Jpn. 51, 463 (1978).

S. Balakrishnan and A. J. Easteal, Aust. J. Chem. 34, 933, 943 (1981).

H. Langhals, Nouv. J. Chim. 5, 97, 115 (1981); ibid. 6, 265 (1982).

I. A. Koppel and J. B. Koppel, Organic Reactivity (Tartu) 20, 547 (1983); Chem. Abstr. 101, 110274 d (1984).

H. Elias, G. Gumbel, S. Neitzel, and H. Volz, Z. Anal. Chem. 306, 240 (1981).

I. A. Koppel and J. B. Koppel, Organic Reactivity (Tartu) 20, 523 (1983); Chem. Abstr. 101, 110180 v (1984).

V. Bekarek and T. Nevecna, Coll. Czech. Chem. Commun. 50, 1928 (1985); ibid. 51, 1942, 2071 (1986).

J. Hicks, M. Vandersall, Z. Babrogic, and K. B. Eisenthal, Chem. Phys. Lett. 116, 18 (1985).

P. Nagy and R. Herzfeld, Acta Universitatis Szegediensis. Acta Physica et Chimica 31, 736 (1985); Chem. Abstr. 107, 22905d (1987).

H. Langhals, Tetrahedron Lett. 27, 339 (1986); Z. Phys. Chem. (Leipzig) 286, 91 (1987).

H. Langhals: Polarität binärer Flüssigkeitsgemische. Angew. Chem. 94, 739 (1982); Angew. Chem., Int. Ed. Engl. 21, 724 (1982).

TABLE I $E_T$ values for different solvents.

| Solvent | $E_N$ |
|---|---|
| n-Hexane | 0.009 |
| Cyclohexane | 0.006 |
| Cyclohexanone | 0.281 |
| Cyclohexanol | 0.500 |
| Ethanol | 0.654 |
| Acetic acid | 0.648 |
| Ethanol/Water (80:20) | 0.710 |
| Methanol | 0.762 |
| Water | 1.000 |

The inventors realized that in order to coordinate and solvate the ionic with the non-ionic species, and separate them without complications in the two aforementioned phases:

they should use a mixture of polar solvent with a less polar solvent, in a manner that an initial single liquid phase would be formed and become two separate liquid phases without much difficulty at a later stage;

the two liquid phases after their formation should be such that one phase would contain substantially the totality of the catalyst, and the other phase would contain at least the majority of the rest of the ingredients;

the solvents used should not introduce foreign matter into the reaction path.

The inventors also realized that in order to achieve the final two-liquid phase system, with substantially no formation or presence of solids during the operation, wherein the catalyst would be in one liquid phase, substantially in its totality, and at least the major part of the components present in the reaction mixture would be in the other liquid phase, one should use more than one solvent, and preferably a combination of at least two solvents.

In selecting the most appropriate solvents for the operation of this invention, the inventors examined all the above criteria for the solvents to induce the formation of the two liquid phases. Considering a combination of just two solvents for this operation, the inventors further realized that in order to achieve a single liquid phase, the two solvents would have to be soluble in each other;

in order for the solvents to form two liquid phases at a later step, the solvents should have to be only partially soluble in each other, so that by exceeding the solubility of one solvent in the other a second liquid phase would necessarily be formed;

in order for substantially the totality of the catalyst ions to move to and reside in one of the two solvents, this one solvent would have to be an extremely polar solvent, such as a protic solvent having a normalized solvent polarity parameter $E_N$ in the range of 0.9 to 1.0, for example; solvents with lower polarity corresponding to an $E_N$ value lower than 0.9 would not attract adequately the very polar catalyst metal ions, resulting in a distribution of the metal ions in the two liquid phases;

in order for the major part of the rest of the components (after removal of the majority of the adipic acid and substantially the totality of the monobasic acid solvent) to move in and reside with the second solvent, this second solvent would have to be considerably less polar than the first one, such as a dipolar aprotic solvent having a normalized solvent polarity parameter $E_N$ in the range of 0.2 to 0.4, for example; solvents characterized by $E_N$ values higher than 0.4 are polar enough to start attracting the catalyst metal ions and thereby effect a distribution of ions between the two phases; solvents characterized by $E_N$ values lower than 0.4 are prone to cause problems with solvent insolubility;

catalyst solids precipitation would occur if the dipolar aprotic solvent (having a normalized solvent polarity parameter $E_N$ in the range of 0.2 to 0.4) would be used as the only solvent;

in order to avoid catalyst precipitation in solid form during the operation, an adequate amount of protic polar solvent (having a normalized solvent polarity parameter $E_N$ in the range of 0.9 to 1.0) would have to be present, with the dipolar aprotic solvent (having a normalized solvent polarity parameter $E_N$ in the range of 0.2 to 0.4);

two-liquid phase formation can be induced by lowering the temperature;

two-liquid phase formation can be induced by adding additional protic solvent, thus deviating from the mutual solubility region of the two solvents;

two-liquid phase formation can be induced by adding an apolar aprotic solvent having a $E_N$ value in the range of 0.0 to 0.1;

working within but close to the border of solubility of one solvent in the other solvent is important, because small additional amounts of the one solvent to the other solvent, or small changes in temperature, will induce formation of a two liquid phases;

in order to minimize the amounts of protic solvent and dipolar aprotic solvent needed for the operation of the present invention, a preceding step of removing a large portion of the non-catalyst solids is highly desirable, since larger amounts of solids require larger amounts of solvents to stay in solution; thus, it is preferable to remove the major part of the adipic acid before proceeding with the following steps.

The inventors found that the reaction mixture obtained after oxidation of cyclohexane to adipic acid to a desired degree of conversion, and after removal of the remaining cyclohexane, the majority (more than 50% by weight) of adipic acid, and even substantially all (more than 95%) the monobasic acid solvent, such as acetic acid for example, may be maintained in a solids-free, monophasic liquid state even after addition of a dipolar aprotic liquid, as long as a protic solvent in an adequate amount is present, both during the removal of the monobasic acid solvent and the addition of the dipolar aprotic solvent. The catalyst may then be separated by formation of an additional solids-free liquid protic phase by the methods described earlier, such as lowering the temperature, or addition of protic solvent, or addition of apolar aprotic solvent, etc. The newly formed protic liquid phase, containing substantially all the catalyst, is thereafter preferably returned to the reaction chamber with or without any further treatment. Thus, this process utilizes a novel manipulation of solvents in order to achieve the separation of the catalyst from the reaction mixture in a concentrated liquid form.

Highly preferred solvents fulfilling the above mentioned conditions in providing a unique two-solvent system were found by the inventors to be:

water as a protic solvent having an $E_N$ value of 1.000 (maximum in the scale); and cyclohexanone as a dipolar aprotic solvent, having a $E_N$ value of 0.281.

In the case that acetic acid is the monobasic acid solvent, it was found by the inventors, very unexpectedly, that substantially complete removal of acetic acid (over 95%) from the reaction mixture, after substantial removal of the cyclohexane, may be achieved without catalyst precipitation by distillation with intermittent or continuous addition of minor amounts of water during the distillation. This was rather unexpected, since the boiling point of water is much lower than that of the acetic acid. Without the addition of water, heavy precipitation occurs during final removal of the acetic acid. When this embodiment of the invention is used, it is highly preferable that at least the majority of the adipic acid has been removed before the substantially complete removal of the acetic acid.

The removal of the acetic acid at this stage is critical in the substantially complete separation of the catalyst from the liquid dipolar aprotic phase to the liquid protic phase. If the removal of the acetic acid is such that the residual acetic acid remaining after distillation is more than about 20% by weight, increasing amounts of catalyst remain in the dipolar aprotic phase, as the removal of acetic acid becomes less and less complete. It seems that removal of acetic acid to at least such a degree is essential because acetic acid, if present at higher levels, distributes itself within both liquid phases and drives them into closer polarity with respect to each other. This results in considerably less complete separation of the catalyst ions to the protic liquid phase from the rest of the mixture (dipolar aprotic liquid phase). In addition, it makes the protic phase more difficult to separate from the dipolar aprotic phase, often necessitating means beyond a decanter, such as for example centrifugation, heating, use of de-emulsifiers, etc. It is most preferable that the removal of the acetic acid is substantially complete (more than 95%) in order to increase as much as possible the polarity difference between the two phases.

One preferred way to separate the catalyst from the solids-free single liquid phase is to maintain such a balance between the dipolar aprotic solvent and the protic solvent, that lowering the temperature to 15° C.–50° C. from a temperature in the range of 80° C.–120° C., causes the formation of an additional protic phase, which contains substantially the totality of the catalyst. The balance of these two solvents may be such that even lowering the temperature to 15° C.–50° C. from a temperature in the range of 80° C.–120° C., does not cause formation of an additional liquid phase, but addition of protic solvent at the lower temperature does, containing again substantially the totality of the catalyst. Further, combination of both most preferred solvents (water and cyclohexanone), according to this invention, constitute a unique solvent system for the efficient separation, and preferably recirculation, of catalyst in a concentrated liquid form.

The solubility of cyclohexanone (CHxO) in water ($H_2O$), and the solubility of water in cyclohexanone are given in Tables II and III, respectively. This data was taken from Gorodetskii I, Ya, Morachevskii A. G., Olevskil V. M., *Vestn. Leningr. Univ, Ser. Mat. Fiz. Khim.* 14, 22 (1959) 136. While in one case, the solubility is favored with increased temperatures, in the other case it is favored with decreased temperatures. The dipolar aprotic solvent, cyclohexanone for example, and the protic solvent, water for example, constitute a novel combination solvent of very desirable and critical characteristics according to this invention.

TABLE II

Solubility of Cyclohexanone in Water

| temp (° C.) | mol % CHxO | mol % $H_2O$ | wt % CHxO |
|---|---|---|---|
| 20 | 1.98% | 98.02% | 10.00% |
| 25 | 1.85% | 98.15% | 9.39% |
| 30 | 1.73% | 98.27% | 8.83% |
| 50 | 1.43% | 98.57% | 7.39% |
| 70 | 1.34% | 98.66% | 6.95% |
| 90 | 1.44% | 98.56% | 7.44% |

TABLE III

Solubility of Water in Cyclohexanone

| temp (° C.) | mol % $H_2O$ | mol % CHxO | wt % $H_2O$ |
|---|---|---|---|
| 20 | 25.1% | 74.9% | 5.7% |
| 25 | 25.6% | 74.4% | 5.9% |
| 30 | 26.1% | 73.9% | 6.0% |
| 50 | 28.7% | 71.3% | 6.8% |
| 70 | 32.6% | 67.4% | 8.1% |
| 90 | 38.5% | 61.5% | 10.2% |

It is very important to point out that the novel combination solvent of this invention, such as the combination of cyclohexanone with water for example, provides an additional synergistic characteristic regarding solubility of various moieties in said combination solvent. This is very significant, especially in the case, in which a highly polar compound, such as for example a metal ion (e.g., cobalt ion), is to be separated from a variety of medium polar compounds dissolved in the novel combination solvent of this invention. More specifically, the products and by-products of the oxidation of cyclohexane to adipic acid have considerably higher solubility in the novel combination solvent of this invention than in each one of the combination solvent's constituents by itself.

At 20° C., adipic acid was found to have a solubility of 1.9% by weight in water, 2% by weight in cyclohexanone, but surprisingly was found to have a solubility higher than 10.4% by weight in a clear solids-free solution containing 4.3 g of succinic acid, 6.9 g of glutaric acid, 11 g of adipic acid, 59.9 g of cyclohexanone, and 24 g of water, which solution had a cyclohexanone to water weight ratio of 2.5. If the solubility of the adipic acid is considered only in terms of the adipic acid, cyclohexanone, and water present, then the solubility of adipic acid in the combination of cyclohexanone and water (having a weight ratio of 2.5) is higher than 11.6%. The statement "higher than" has been used, since it was not examined, in the example, how much more adipic acid would be soluble in the pure combination solvent.

In another example, adipic acid was found to have a solubility higher than 9.6% by weight in a clear solids-free solution containing 5.27 g of succinic acid, 9.61 g of glutaric acid, 7.74 g of adipic acid, 44.12 g of cyclohexanone, and 14.11 g of water, which solution had a cyclohexanone to water weight ratio of 3.1. Again, if the solubility of the adipic acid is considered only in terms of the adipic acid, cyclohexanone, and water present, then the solubility of adipic acid in the combination of cyclohexanone and water (having a weight ratio of 3.1) is higher than 11.7%.

As one can observe, the above solutions contained not only increased amounts of adipic acid, but also additional matter in the form of succinic acid and glutaric acid, which renders these findings even more unexpected.

Another profound phenomenon demonstrated by the above examples is that the solubility of water in cyclohexanone is increased immensely by the presence of the dibasic acids. Table III shows that the solubility of water in cyclohexanone at 20° C. is 5.7% by weight, which corresponds to a cyclohexanone to water weight ratio of 16.5, which is extremely higher than the weight ratios of 2.5 and 3.1 in the above examples.

At the same time, the addition of the novel combination solvent of the present invention in the reaction mixture decreases considerably the solubility of the cobalt ion without insolubilizing it. In the absence of water, addition of cyclohexanone causes immediate precipitation of the cobalt ion.

Further, it is very important to impress that the novel combination solvent includes all forms; for example, the case in which the novel combination solvent exists as a monophasic liquid system in the absence or presence of a solute (such as dibasic acids, esters, etc., for example), the case in which the combination solvent initially exists as a diphasic liquid system in the absence or presence of a solute, the case in which the combination solvent is formed during a solution is being formed, and the case in which the combination solvent is formed after a solution has already been formed. The novel combination solvent comprises the totality of the dipolar aprotic and the protic solvents.

The above profound and unexpected attributes (considerable increase of dibasic acid solubility combined with considerable decrease of cobalt ion solubility in the novel combination solvent) are primarily responsible for a clean separation of the cobalt ion in the water phase from the rest of the reaction mixture, which remains dissolved in the dipolar aprotic solvent phase of the instant invention.

Referring now to FIG. 1, there is depicted a reactor assembly or device 10, comprising a reaction chamber 12 connected to a first evaporator 14 through line 12$i$. Connected to the reaction chamber 12, there is a feeding line 12', which is shown as a single line for purposes of clarity and brevity. Feeding line 12' may comprise more than one feeding lines along with other appropriate equipment well known to the art, such as for example heaters, mixers, etc. The feeding line 12' is used to feed raw materials, as well as recycled materials from the process.

The reaction chamber 12 is also preferably connected to a first condenser 18 through line 12$ii$, which first condenser 18 is preferably connected to a decanter 20 through line 18$i$. The decanter 20 is connected to line 20$i$, which may partially lead back to the reaction chamber 12 and/or to a treatment station (not shown), and to line 20$ii$, which preferably leads back to the reaction chamber 12.

The first evaporator 14 is connected to a first crystallizer/separator 22 through line 14$i$, and to a second condenser 24 through line 14$ii$. The second condenser 24 is in turn connected to a second decanter 26 through line 24$i$. The second decanter 26 is connected to a line 26$i$, and to line 26$ii$, either one of which may lead to the reaction chamber 12 or to any other appropriate chamber(s).

The first crystallizer/separator 22 may actually comprise more than one chambers (not individually shown for purposes of clarity), such as for example cooler(s), crystallizer(s), recrystallizer(s), wash stations, separator(s), such as for example centrifugal separator(s) and/or filter(s), all very well known to the art.

The first crystallizer/separator 22 is connected to a second evaporator 27 through line 22$i$, as well as to line 22$ii$ through which crystallized and/or recrystallized and/or purified matter exits the crystallizer/separator 22.

The second evaporator 27 is connected to a mixer 28 through line 27$i$, as well as to solvent removal line 27$ii$. An additive line 27' is connected to the second evaporator 27.

The mixer 28 is connected to a catalyst separator/decanter 30 through line 28$i$. Feeding lines 28', 28" and 28'" are connected to the mixer 28. The feeding lines 28', 28" and 28'" are suitable to introduce solvents to the mixer 28.

Line 28$i$ may contain a cooler (not shown), the purpose of which is to cool the stream of said line 28$i$ to a lower temperature.

The catalyst separator/decanter 30 is connected to a third evaporator 34 through line 30$i$, and to a catalyst treatment station 32 through line 30$ii$. A solvent addition line 30' is connected to the catalyst separator/decanter 30.

The catalyst treatment station 32 is preferably connected (not shown for purposes of clarity) back to the reaction chamber 12 through line 32$i$. The catalyst treatment station 32 is also preferably connected to a solvent removal line 32". An additive line 32' is connected to the catalyst treatment station 32.

The third evaporator 34 is connected to a hydrolysis station 36 through line 34$i$, and to a solvent removal line 34$ii$.

The hydrolysis station 36 is connected to a fourth evaporator 38 through line 36$i$. An additive line 36' is connected to the hydrolysis station 36.

The fourth evaporator 38 is connected to a second crystallizer/separator 40 through line 38$i$. The fourth evaporator 38 is also connected to a solvent removal line 38$ii$.

The second crystallizer/separator 40 is connected through line 40$i$ to a further treatment station (not shown for purposes of clarity) and/or to an appropriate disposal station (also not shown for purposes of clarity). The second crystallizer/separator 40 is also connected to line 40$ii$ for removal of matter crystallized and/or recrystallized and/or purified in the second crystallizer/separator 40. The matter removed through line 40$ii$ may be recycled to the first evaporator 14

In operation of this embodiment, raw materials, including an oxygen containing gas, as well as recycled matter enter the reaction chamber 12 through feeding line 12'. As explained earlier, the feeding line 12' represents in general a number of lines or a combination of lines and miscellaneous devices, well known to the art. Preferably, the reaction in the reaction chamber 12 takes place at a temperature in the range of 80° to 120° C., and more preferably, at a temperature in the range of 90° to 110° C. For safety purposes, it is highly preferable that the volume percent of oxygen in the reaction chamber 12, in the condenser 18, and the decanter 20 is below the lower flammability limit. The oxygen partial pressure is preferably maintained in a range above a value which renders the reaction oxygen limited.

The heat of reaction may be removed as shown in FIG. 1 by the first condenser 18, which first condenser 18 may be used by itself, in which case all the condensed matter returns to the reaction chamber 12 at a lower temperature than the temperature of the contents of the reaction chamber 12. The condenser 18 may also be used in combination with the first decanter 20, in which case the condensed matter is separated in the first decanter 20 by formation of a lower polar phase containing mainly water with some acetic acid, and an upper non-polar phase, which contains mainly cyclohexane with some acetic acid and a minute amount of water. Of course, a part of the condensate may be fed to the decanter, and a part directly to the reaction chamber.

The non-polar phase may preferably be directed back to the reaction chamber 12 through line 20ii, while only part or none of the polar phase is returned to the reaction chamber 12 through line 20i. The amount of the polar phase returned to the reaction chamber 12 is preferably regulated by a controller, preferably a computerized controller (not shown for purposes of clarity), to be lower than that which would cause the formation of a second liquid phase in the reaction chamber 12. At the same time, the water concentration in the reaction chamber 12 is regulated by the controller (not shown) to be higher than that which would cause catalyst precipitation in the reaction chamber 12.

Depending on the particular occasion, other cooling devices, such as for example cooling coils (not shown), or cooling jackets (not shown), etc., inside or outside the reaction chamber 12, may be used to remove the heat and control the temperature, by themselves or in combination with condensers and decanters.

The hold up time of the mixture in the reaction chamber 12 is such as to preferably produce and maintain a steady state in a continuous system. The reaction mixture is preferably continuously being transferred to the first evaporator 14, in which the cyclohexane, the water, and part of the monobasic acid solvent, such as acetic acid for example, is removed by evaporation through line 14ii. The evaporated matter in the second condenser 24 is transferred to the second decanter 26, in which it is separated, as in the first decanter 20, by formation of a lower polar phase containing mainly water and acetic acid, and an upper non-polar phase, which contains mainly cyclohexane with some acetic acid and a minute amount of water.

The non-polar phase may preferably directed back to the reaction chamber 12 through line 26ii, while only part or none of the polar phase is returned to the reaction chamber 12 through line 26i. The amount of the polar phase returned to the reaction chamber 12, through line 26i, is preferably regulated by a controller, preferably a computerized controller (not shown for purposes of clarity), to be (in combination with the polar phase returned to the reaction chamber 12 through line 20i) lower than that which would cause the formation of a second liquid phase in the reaction chamber 12. At the same time, the amount of water present in the reaction chamber 12 is regulated by the controller (not shown), as aforementioned, to be higher than that which would cause catalyst precipitation in the reaction chamber 12. Some or all of the polar phase returned to the reaction chamber 12, through line 26i and/or line 26i, may be directed through an intermediate treatment station (not shown) for better control of the water concentration within the reaction chamber 12.

The mixture obtained in the evaporator 14, is then fed to the crystallizer/separator 22, in which it is cooled down and crystallized in a manner that adipic acid is separated in the form of crystals from the rest of the mixture. The crystallized crude adipic acid may be recrystallized for purification, and separated through line 22ii. It is preferable that the crystallization is conducted at a temperature in the range of 15° to 50° C.

The monophasic liquid remaining after the crystallization is directed through line 22i to the second evaporator 27, in which acetic acid is evaporated through line 27ii and optionally fed to a treatment station, mainly for removal of water, or recycled to the reaction chamber 12, or both. The evaporation is preferably conducted under reduced pressure, and at a temperature preferably in the range of 80° to 120° C.

The removal of acetic acid at this point is preferably such that the mixture leaving from the second evaporator 27 through line 27i has an acetic acid content preferably less than 25% by weight and more preferably less than 20%. It is, however, considerably more preferable that the removal of acetic acid is substantially complete (the remaining mixture containing less than 5% by weight of the remaining mixture), in order to absolutely ensure substantially complete separation of catalyst at a later stage.

If the remaining mixture, after evaporation of the acetic acid, still contains about 25% acetic acid by weight, the remaining mixture is still in some instances in the form of a solids-free single liquid phase. This solids-free single liquid phase is viscous, but it can still be easily handled by pumps and other commercial equipment well known to the art. If the removal of acetic acid becomes more complete, particularly in the case that the majority of the adipic acid has not been removed in a previous step, a precipitate will develop, containing catalyst, and most probably dibasic acids, among other moieties, if no special and critical measures are taken. However, a first solids-free single liquid phase will be maintained, even upon substantially complete removal of acetic acid, if a small continuous or intermittent stream of a protic solvent, lacking acid groups and having a normalized solvent polarity value $E_N$ in the range of 0.9 to 1, is introduced to the mixture being subjected to evaporation. An example of such a protic solvent is water, which in addition to its very high $E_N$ value (1.000), will not contaminate the mixture with matter foreign to the process, since water is a by-product of the oxidation of the cyclohexane. Thus, as acetic acid is being evaporated in the second evaporator 27, and leaving said evaporator through line 27ii, a small continuous or intermittent stream of water is being added into the second evaporator 27 through additive line 27'. The fact that catalyst precipitation is prevented by the addition of small amounts of water is unexpected, since the boiling point of water is considerably lower than the boiling point of acetic acid. One would expect that the water would be leaving the system as soon as introduced into the evaporator, and therefore, would have no effect on the formation or non-formation of a solid phase; but this is not the case. Prevention of formation of a solid phase, especially catalyst, is highly desirable and vital, since it prevents plugging problems, use of expensive equipment, serious difficulties in handling, etc.

The mixture treated in this manner is transferred to the mixer 28, into which the novel combination solvent is added resulting in a second solids-free single liquid phase of considerably lower viscosity than the first solids-free single liquid phase in the second evaporator 27. The novel combination solvent, as aforementioned, comprises a dipolar aprotic solvent having a normalized solvent polarity parameter $E_N$ in the range of 0.2 to 0.4, and the same or similar protic solvent that was used in the previous step. Again, water is the highly preferable protic solvent for the reasons discussed above. Regarding the dipolar aprotic solvent having a normalized solvent polarity parameter $E_N$ in the range of 0.2 to 0.4, cyclohexanone is the most preferred solvent, since it is an intermediate and/or raw material in the process and therefore not a source of contamination.

The solvents described above may be introduced into the mixer 28 either in one stream or in more streams or individually. Further, if an adequate amount of protic solvent has been added in the evaporator 27 to suffice in quantity, with regard to prevention of a solids phase formation, when the mixture is in the mixer, then addition of protic solvent in the mixer is obviously not necessary. The preferable ratios at which the miscellaneous solvents are used have already been discussed at an earlier section. In any event, it is preferable that the minimum amounts of solvents are used. The temperature in the mixer 28 is preferably maintained in the range of 80° C. to 120° C.

From the mixer 28, the second solids-free single liquid phase is fed to the catalyst separator/decanter 30. The stream of the second solids-free single liquid phase may pass through a cooler (not shown), as mentioned above, so that the temperature is lowered to a desired degree, preferably in the range of 15° C. to 50° C.

Depending on the proportions of the dipolar aprotic solvent and the protic solvent in the second solids-free single liquid phase, an additional new solids-free liquid phase may be formed upon cooling, which contains substantially the totality of the catalyst. If at the higher temperature the amount of protic solvent is close to the solubility limit of protic solvent in the mixture, the formation of an additional liquid phase as the temperature decreases is imminent.

If the proportions of the dipolar aprotic solvent and the protic solvent in the second solids-free single liquid phase are such (the amount of protic solvent is considerably lower than the solubility limit of the protic solvent in the second solids-free single liquid phase) that with the cooling no additional new solids-free liquid phase is formed, or if no cooling takes place, addition of adequate amounts of protic solvent, preferably water, through line 30', causes formation of the additional protic phase, which contains substantially the totality of the catalyst. Thus, the protic solvent separates substantially the totality of the catalyst, preferably cobalt ions, as cobalt succinate, glutarate, and adipate and/or acetate, in a solution form. Succinic acid is most prone to bind to the cobalt ions, then glutaric acid, then adipic acid and then acetic acid, particularly in the case that substantially all the acetic acid has been removed.

It is very important to note that, under steady state conditions, the catalyst salts separated in the catalyst separator/decanter 30 in the form of solution, and the catalyst salts added (coming from the catalyst separator/decanter 30) to the reaction chamber 12 are the same for all practical purposes, and therefore their material balance remains constant, and no built-up of any sort may occur.

Addition of aprotic apolar solvent, such as cyclohexane for example, may also be made in small quantities through line 30', for facilitating the formation of the additional liquid phase, which contains the catalyst. Caution must be exercised, however, to avoid addition of excessive amounts of aprotic apolar solvent, especially in the case the large quantities of adipic acid are present, because precipitation of adipic acid may occur.

The separated or decanted protic phase coming out through line 30ii is preferably treated at the catalyst treatment station 32, at which at least the majority of the protic solvent is removed, by evaporation for example, through line 32ii. Monobasic acid solvent, such as acetic acid for example, is added through line 32', and a solution of the catalyst salts in the monobasic acid solvent is returned to the reaction chamber 12 through line 32i. Although this type of treatment is highly preferable, a very important part is to keep the protic solvent content in the reaction chamber 12 at low enough levels in order to avoid formation of a second liquid phase, and at the same time higher than that at which or under which catalyst precipitates.

The catalyst treatment station 32 may preferably comprise at least two separate sub-stations (not shown), one of which serves for at least partial removal of water through line 32ii, the other one serving for the addition of the monobasic acid solvent through line 32'.

The water which is removed through line 32ii may be preferably recycled to the catalyst separator/decanter 30, preferably through line 30'.

The dipolar aprotic phase leaving the catalyst separator/decanter 30 through line 30i is fed to the third evaporator 34, wherein the dipolar aprotic solvent, which was added in the mixer 28, is evaporated through line 34ii, and preferably is recycled to the mixer 28. In the case of such recycling, protic solvent, also present in the third evaporator 34, evaporated along with the dipolar aprotic solvent through line 34ii minimizes the amount of fresh protic solvent added in the mixer 28.

The mixture remaining after the dipolar aprotic solvent is removed, is directed to the hydrolysis chamber 36 through line 34i. The hydrolysis chamber 36 preferably contains a solid acidic hydrolysis catalyst, such as Nafion® for example. Water is added to the hydrolysis chamber 36 through line 36'. The hydrolysis may be conducted by techniques well known to the art, at atmospheric or raised pressure, and temperatures preferably in the vicinity of 100° C. or higher. A combination of hydrothermal and catalytic hydrolysis is preferable according to this invention.

The hydrolyzed mixture is directed to the fourth evaporator 38 through line 36i, where it is concentrated by removing water. The concentrated mixture is directed to the second crystallizer/separator 40, where it is cooled, resulting in crystallization of adipic acid, much of which is released by the hydrolysis in chamber 36 and some of which remains in the liquid phase after the initial crystallization in chamber 22. The adipic acid crystallized in crystallizer/separator 40, is then separated, optionally recrystallized, etc. The adipic acid is in turn removed through line 40ii. The remaining mother liquor is driven, through line 40i, for further treatment and/or appropriate disposal. The further treatment may comprise separation and recycling of underoxidized species, separation and/or esterification of dibasic acids, etc.

It should be understood that any combinations of the exemplifying embodiments, in part or in total, or any equivalent arrangements or any combinations of equivalent arrangements may be utilized, and are within the scope of the present invention.

Although miscellaneous functions are preferably controlled by a computerized controller, it is possible, according to this invention, to utilize any other type of controller or even manual controls and/or labor for controlling one or more functions. Preferred computerized controllers include artificially intelligent systems (expert systems, neural networks, and fuzzy logic systems, well known to the art). Of the three types of the artificially intelligent systems, the neural network, which is a learning system, collects information from different places of the device (for example pressure, temperature, chemical or other analysis, etc.), stores this information along with the result (pressure drop rate, reaction rate, reactivity, and the like, for example), and is programmed to use this information in the future, along with other data if applicable, to make decisions regarding the action to be taken at each instance. The expert systems are programmed based on the expertise of experienced human beings. The fuzzy logic systems are based on intuition rules in addition to expertise rules.

In more general nomenclature of phases, "polar phase" is the more polar phase, while "non-polar" phase is the less polar phase. Thus in this case, the polar phase is the protic phase, while the non-polar phase is the dipolar aprotic phase.

Oxidations according to this invention, are non-destructive oxidations, wherein the oxidation product is different than carbon monoxide, carbon dioxide, and a mixture thereof, such as adipic acid for example. Of course, small amounts of these compounds may be formed along with the oxidation product, which may be one product or a mixture of products.

Regarding adipic acid, the preparation of which is especially suited to the methods of this invention, general information may be found in a plethora of U.S. Patents, among other references. These include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Diacids or other suitable compounds may be reacted, according to well known techniques to the art, with a reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers. Furthermore, additives may be combined with the polymers and/or fibers, where fillers are one type of additive, to thereby form a composite. Thus, the methods of the present invention may include a step of polymerizing the adipic acid of this process as described above to form polymers and fibers, as well as adding to the polymer (or fiber) fillers and/or other additives to form composites, and a combination thereof.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof. Furthermore, any attempted explanations in the discussion are only speculative and are not intended to narrow the limits of this invention.

What is claimed is:

1. A method of treating a reaction mixture produced by direct oxidation of cyclohexane to adipic acid, the reaction mixture comprising cyclohexane, adipic acid, a monobasic acid solvent having only primary and/or secondary hydrogen atoms, optionally water, and a metal ion catalyst, the method being characterized by steps of:

(a) removing greater than 95% of the cyclohexane;

(b) removing a major part of the adipic acid;

(c) removing greater than 95% of the monobasic acid solvent by distillation, during which a protic solvent is added continuously or intermittently to provide a first single liquid phase, the first single liquid phase being homogeneous and solids-free, the protic solvent containing no carboxylic or mineral acid groups and having a normalized solvent polarity parameter $E_N$ in the range of 0.9 to 1.0;

(d) adding to the first single liquid phase, a dipolar aprotic solvent and, if needed, additional protic solvent, in such quantities so as to provide a second single liquid phase that is homogeneous and solids-free at a desired first temperature, the dipolar aprotic solvent having a normalized solvent polarity parameter $E_N$ in the range of 0.2 to 0.4;

(e) causing formation of two liquid phases, a solids-free protic liquid phase containing greater than 95% of the metal ion catalyst, and a solids-free aprotic liquid phase containing at least the majority of products and by-products of the reaction mixture by a process selected from a group consisting of lowering the first temperature to a second temperature, adding additional protic solvent, adding an apolar aprotic solvent having a $E_N$ value in the range of 0.0 to 0.1, and a combination thereof; and (f) separating the solids-free protic liquid phase containing the catalyst from the solids-free aprotic liquid phase;

wherein $E_N$ is defined by equation (1)

$$E_N = \frac{E_T(\text{solvent}) - E_T(\text{TMS})}{E_T(\text{water}) - E_T(\text{TMS})} = \frac{E_T(\text{solvent}) - 30.7}{32.4} \quad (1)$$

using water and tetramethylsilane as extreme reference solvents, such that $E_T$ (solvent) is the $E_T$ value corresponding to the solvent under consideration, $E_T$ (TMS) is the $E_T$ value corresponding to tetramethylsilane, and $E_T$ (water) is the $E_T$ value corresponding to water, and wherein $E_T$ is defined by equation (2)

$$E_T/(\text{kcal}\cdot\text{mol}^{-1}) = h\cdot c\cdot v\cdot N_A = 2.859\times10^{-3}\cdot v/\text{cm}^{-1} \quad (2)$$

in which v is the wavenumber ($\text{cm}^{-1}$) of the photon which produces the electronic excitation, h is Plank's constant, c is the velocity of light, and $N_A$ is Avogadro's Number, $E_T$ being based either directly on the transition energy for the longest wavelength solvatochromic absorption band of pyridinium-N-phenoxide betaine dye in the solvent under consideration, or indirectly by the use of the more lipophilic penta-tert-butyl-substituted pyridinium-N-phenoxide betaine dye in the solvent under consideration.

2. A method as defined in claim 1, wherein the weight ratio of the first single liquid phase to the total protic solvent used in steps (c) and (d), is in the range of 1 to 3.

3. A method as defined in claim 2, wherein the weight ratio of the dipolar aprotic solvent to the first single liquid phase is in the range of 1 to 3.

4. A method as defined in claim 1, wherein the weight ratio of the dipolar aprotic solvent to the first single liquid phase is in the range of 1 to 3.

5. A method as defined in claim 3 wherein the first temperature is in the range of 80° C. to 120° C.

6. A method as defined in claim 5 wherein the second temperature is in the range of 15° C. to 50° C.

7. A method as defined in claim 6 wherein steps (a) and (b) precede steps (c), (d), (e), and (f).

8. A method as defined in claim 7, further comprising a step of recycling the solids-free protic liquid phase to a reaction zone, in which reaction zone the cyclohexane is oxidized to adipic acid, either directly or indirectly, and/or with or without removal of protic solvent, and/or with or without addition of monobasic acid solvent.

9. A method as defined in claim 7, further comprising a step of hydrolyzing esters contained in the solids-free aprotic liquid phase.

10. A method as defined in claim 1 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

11. A method as defined in claim 2 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

12. A method as defined in claim 3 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

13. A method as defined in claim 4 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

14. A method as defined in claim 5 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

15. A method as defined in claim 6 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

16. A method as defined in claim 7 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

17. A method as defined in claim 8 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

18. A method as defined in claim 9 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

19. A method of separating catalyst in a solution form from a reaction mixture produced by direct oxidation of cyclohexane to adipic acid, the reaction mixture comprising cyclohexane, adipic acid, a monobasic acid solvent having only primary and/or secondary hydrogen atoms, optionally water, and a metal ion catalyst, the method being characterized by steps of:

(a) removing greater than 95% of the cyclohexane;

(b) optionally removing a major part of the adipic acid;

(c) removing monobasic acid solvent to provide a first solids free single liquid phase containing less than about 20% by weight of the monobasic acid solvent;

(d) adding, to the first single liquid phase, a dipolar aprotic solvent and, if needed, additional protic solvent, in such quantities so as to provide a second single liquid phase that is homogeneous and solids-free at a desired first temperature, the dipolar aprotic solvent having a normalized solvent polarity parameter $E_N$ in the range of 0.2 to 0.4;

(e) causing formation of two liquid phases, a solids-free protic liquid phase containing substantially all the metal ion catalyst, and a solids-free aprotic liquid phase containing at least the majority of products and by-products of the reaction mixture by a process selected from a group consisting of lowering the first temperature to a second temperature, adding additional protic solvent, adding an apolar aprotic solvent having a $E_N$ value in the range of 0.0 to 0.1, and a combination thereof; and (f) separating the solids-free protic liquid phase containing the catalyst from the solids-free aprotic liquid phase;

wherein $E_N$ is defined by equation (1)

$$E_N = \frac{E_T(\text{solvent}) - E_T(\text{TMS})}{E_T(\text{water}) - E_T(\text{TMS})} = \frac{E_T(\text{solvent}) - 30.7}{32.4} \quad (1)$$

using water and tetramethylsilane as extreme reference solvents, such that $E_T(\text{solvent})$ is the $E_T$ value corresponding to the solvent under consideration, $E_T(\text{TMS})$ is the $E_T$ value corresponding to tetramethylsilane, and $E_T(\text{water})$ is the $E_T$ value corresponding to water, and wherein $E_T$ is defined by equation (2)

$$E_T/(\text{kcal·mol}^{-1}) = h \cdot c \cdot v \cdot N_A = 2.859 \times 10^{-3} \cdot v/\text{cm}^{-1} \quad (2)$$

in which v is the wavenumber ($\text{cm}^{-1}$) of the photon which produces the electronic excitation, h is Plank's constant, c is the velocity of light, and $N_A$ is Avogadro's Number, $E_T$ being based either directly on the transition energy for the longest wavelength solvatochromic absorption band of pyridinium-N-phenoxide betaine dye in the solvent under consideration, or indirectly by the use of the more lipophilic penta-tert-butyl-substituted pyridinium-N-phenoxide betaine dye in the solvent under consideration.

20. A method as defined in claim 19, wherein the weight ratio of the first single liquid phase to the total protic solvent used in steps (c), and (d), is in the range of 1 to 3.

21. A method as defined in claim 19, wherein the weight ratio of the dipolar aprotic solvent to the first single liquid phase is in the range of 1 to 3.

22. A method as defined in claim 20, wherein the weight ratio of the dipolar aprotic solvent to the first single liquid phase is in the range of 1 to 3.

23. A method as defined in claim 22 wherein the first temperature is in the range of 80° C. to 120° C.

24. A method as defined in claim 23 wherein the second temperature is in the range of 15° C. to 50° C.

25. A method as defined in claim 24 wherein steps (a) and (b) precede steps (c), (d), (e), and (f).

26. A method as defined in claim 24, further comprising a step of recycling the solids-free protic liquid phase to a reaction zone, in which reaction zone the cyclohexane is oxidized to adipic acid, either directly or indirectly, and/or with or without removal of protic solvent, and/or with or without addition of monobasic acid solvent.

27. A method as defined in claim 24, further comprising a step of hydrolyzing esters contained in the solids-free aprotic liquid phase.

28. A method as defined in claim 19 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

29. A method as defined in claim 20 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

30. A method as defined in claim 21 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

31. A method as defined in claim 22 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

32. A method as defined in claim 23 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

33. A method as defined in claim 24 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

34. A method as defined in claim 25 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

35. A method as defined in claim 26 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

36. A method as defined in claim 27 wherein the monobasic acid solvent comprises acetic acid, the protic solvent comprises water, the metal ion catalyst comprises cobalt ions, the dipolar aprotic solvent comprises cyclohexanone, and the apolar aprotic solvent comprises cyclohexane.

\* \* \* \* \*